(12) United States Patent
Vieth

(10) Patent No.: US 10,188,677 B2
(45) Date of Patent: Jan. 29, 2019

(54) IRON SUPPLEMENT COMPOSITION

(75) Inventor: Reinhold Vieth, Toronto (CA)

(73) Assignee: THE D DROPS COMPANY INC., Woodbridge (CA)

( * ) Notice: Subject to any disclaimer, the term of this patent is extended or adjusted under 35 U.S.C. 154(b) by 0 days.

(21) Appl. No.: 14/131,070

(22) PCT Filed: Jul. 5, 2012

(86) PCT No.: PCT/CA2012/000639
§ 371 (c)(1),
(2), (4) Date: Apr. 24, 2014

(87) PCT Pub. No.: WO2013/003947
PCT Pub. Date: Jan. 10, 2013

(65) Prior Publication Data
US 2014/0234437 A1    Aug. 21, 2014

(30) Foreign Application Priority Data
Jul. 5, 2011 (CA) ...................... 2745267

(51) Int. Cl.
*A61K 33/26* (2006.01)
*A61K 9/00* (2006.01)
(Continued)

(52) U.S. Cl.
CPC ............... *A61K 33/26* (2013.01); *A23D 9/00* (2013.01); *A23L 33/15* (2016.08); *A23L 33/155* (2016.08);
(Continued)

(58) Field of Classification Search
CPC .......... A23L 1/3006; A61K 33/26; A61K 9/10
(Continued)

(56) References Cited

U.S. PATENT DOCUMENTS 5,120,527 A     6/1992 Li et al.
2009/0317488 A1*  12/2009 Mehta et al. ................. 424/648
(Continued)

FOREIGN PATENT DOCUMENTS

CA    2558202 A1   11/2006
CA    2578881       7/2007
(Continued)

OTHER PUBLICATIONS

Choe, E. et al. "Mechanisms and factors for edible oil oxidation", Compr Rev Food Sci Food Saf, Sep. 2006, vol. 5, Issue 4, pp. 169-186. (Year: 2006).*

(Continued)

*Primary Examiner* — Gina C Justice
(74) *Attorney, Agent, or Firm* — Katten Muchin Rosenman LLP

(57) ABSTRACT

In one of its aspects, the present invention provides a composition comprising: (i) a non-encapsulated iron salt, and (ii) a carrier comprising digestible edible oil that is a liquid at 20° C. This composition advantageously provides iron in a form that is easily administered to an infant or adult. When taken directly by mouth or added to food or infant formula, the composition has a desirably bland flavor and is easy to consume. Moreover, the high density of iron per unit volume of the composition results in a minimal volume of liquid to be administered. This makes the composition relatively innocuous and easy for infants to consume. Related aspects of the present invention are also described—e.g., uses, articles of manufacture and the like.

12 Claims, 1 Drawing Sheet

(51) Int. Cl.
*A61K 9/10* (2006.01)
*A61K 31/295* (2006.01)
*B65D 47/18* (2006.01)
*A23D 9/00* (2006.01)
*A23L 33/15* (2016.01)
*A23L 33/155* (2016.01)
*A23L 33/16* (2016.01)

(52) U.S. Cl.
CPC ............ *A23L 33/16* (2016.08); *A61K 9/0041* (2013.01); *A61K 9/10* (2013.01); *A61K 31/295* (2013.01); *B65D 47/18* (2013.01); *A23V 2002/00* (2013.01)

(58) Field of Classification Search
USPC .......................................................... 424/647
See application file for complete search history.

(56) References Cited

U.S. PATENT DOCUMENTS

| | | | |
|---|---|---|---|
| 2009/0317517 A1 | 12/2009 | van Kempen et al. | |
| 2010/0021563 A1* | 1/2010 | Levesque ................ | A61K 8/27 424/642 |
| 2010/0203160 A1* | 8/2010 | Bydlon et al. ................ | 424/638 |

FOREIGN PATENT DOCUMENTS

| | | |
|---|---|---|
| GB | 759577 A | 10/1956 |
| JP | 09-205988 A | 8/1997 |
| JP | H09-205988 A | 8/1997 |
| WO | 00/72831 A1 | 12/2000 |
| WO | 20051073355 A1 | 8/2005 |
| WO | 2005/112654 A2 | 12/2005 |

OTHER PUBLICATIONS

International Search Report for International Application No. PCT/CA2012/000639 dated Sep. 24, 2012.
Extended European Search Report for European Patent Application No. 12 80 7122 dated Nov. 11, 2014.
First Examination Report for New Zealand Patent Application No. 619610, dated Oct. 13, 2014.
International Report on Patentability for International Application No. PCT/CA2012/000639, dated Jan. 7, 2014.
English translation of Notification of the First Office Action and the Search Report for Chinese Application No. 2012800335697, and the search report in Chinese, dated May 5, 2015.
Office Action for European Patent Application No. 12 807 122.2 dated Jan. 19, 2018.

* cited by examiner

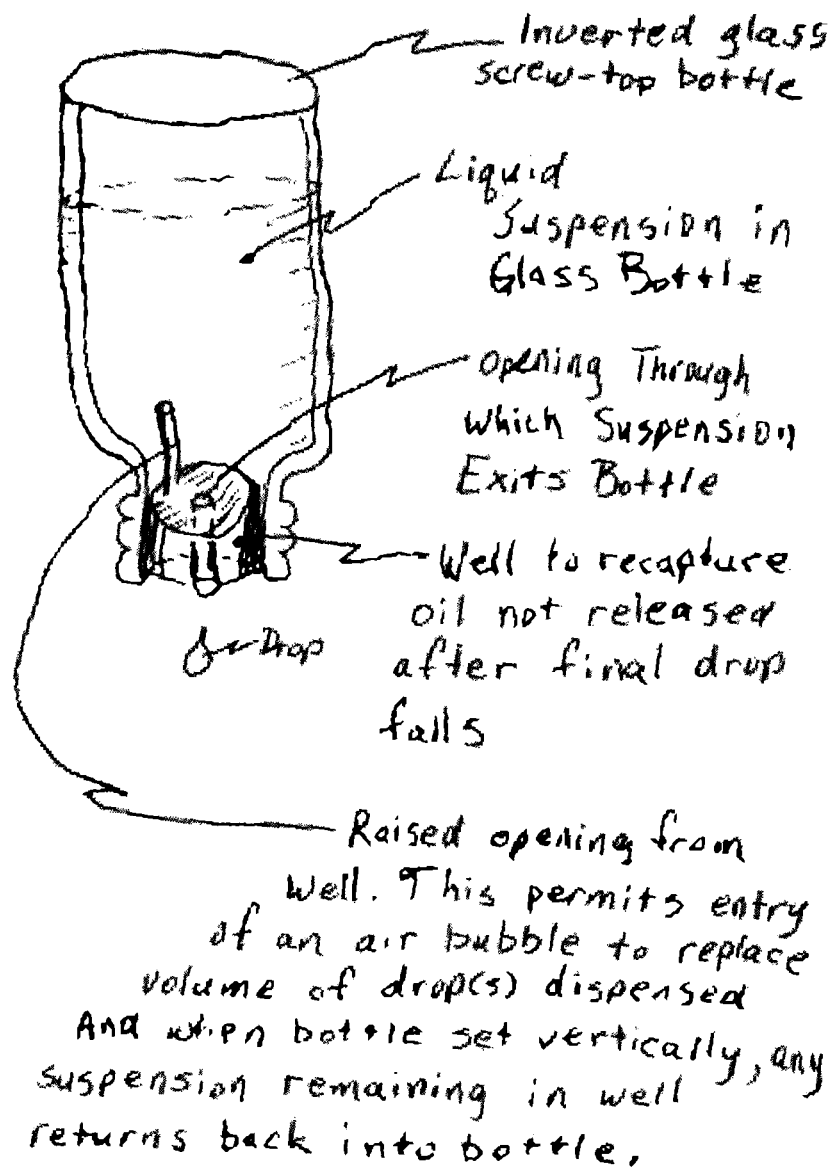

IRON SUPPLEMENT COMPOSITION

FIELD OF THE INVENTION

In one of its aspects, the present invention relates to a composition particularly useful as a dietery supplement, more particularly as dietery iron (Fe) supplement. In another of its aspects, the present invention relates to use of the composition as a dietery supplement, for example to prevent or treat iron deficiency in a human.

DESCRIPTION OF THE PRIOR ART

Iron is a known and necessary nutrient that is involved in the proper function of enzymes involved in energy transfer. Iron is also a component of hemoglobin and myoglobin—i.e., components of blood that are used to transport oxygen.

Iron deficiency anemia is the most common nutrient deficiency in the world. The condition is readily treatable with an iron supplement. Iron deficiency even without the manifestation of anemia can harm infants because iron deficiency can impair neurodevelopment and behavior, some of which may be irreversible.

A guidance document from the American Academy of Pediatrics (2010) highlights the importance of iron-deficiency anemia, and it summarizes commercially available iron supplements. Although breast-feeding is the ideal way to feed infants through most of the first year of life, an infant's iron store acquired from the mother while in the womb is usually depleted by about 4 to 6 months of age. Iron supplements are often given to infants, but it is well known that iron supplements are not given or taken as often as is needed.

Commercially available iron supplement products are known. Typically, these are products that, when available for use with infants, are in in the form of drops comprised, for example, of iron sulfate solution in a water base with glycerine or alcohol, together with optional colors or flavorings. An example of such a commercially available supplement is FER-IN-SOL™. The iron may be in a different form. For example, iron fumarate is available as water-based suspension, under the brand name PLAFER™, and ferrous sulfate is available as a water-based suspension, under the brand name MYKIDZ™. Further, for children and adults, chewable iron tablets are available, for example, FEOSOL™.

Further, iron is a component of many multivitamin pills.

Iron sprinkles, a powder containing micro-encapsulated ferrous fumarate is also known in the prior art. For example, U.S. Pat. No. 6,830,761 [Zlotkin] teaches a composition useful in the prevention of iron deficiency anemia. The composition comprises micro-encapsulated iron granules in combination with a lipid-based excipient. The composition may additionally contain other micronutrients including ascorbic acid, zinc, vitamin A and iodine. Zlotkin teaches that the composition is particularly useful for the prevention of iron deficiency anemia in infants between the ages of 6 and 24 months of age since it can readily be admixed with the semi-solid foods this age group consumes. The importance of using micro-encapsulated iron (i.e., versus non-encapsulated iron) is illustrated in Examples 1 and 2 of Zlotkin. Specifically, it is reported in Example 2 of Zlotkin that there is no significant difference in the hemoglobin response between rats fed similar amounts of iron as the reference compound (i.e., non-encapsulated ferrous sulfate) versus rats fed micro-encapsulated ferrous fumarate. Thus, the use of micro-encapsulated iron is central to the teaching of Zlotkin.

U.S. Pat. No. 6,352,730 [Zimmerman et al. (Zimmerman)] teaches a method of adding food-additive ingredients to a food product, particularly a reduced fat fried snack product, and an ingredient suspension containing a flowable edible, preferably a nondigestible fat, and food-additive ingredients. The method consists of suspending the encapsulated or powdered ingredients in the flowable edible fat, and applying the suspension in a controlled amount to the surface of a food product. The preferred food product is a fabricated reduced fat or fat-free potato chip which is a fried snack made by frying a dough in a nondigestible fat to a moisture content of less than 5%. The ingredient suspension is applied to the surface of the fried snack soon after emerging from the fryer. Zimmerman states that the food product has a light, crispy, improved crunchy texture, improved flavor and a fat content of from about 20% to about 38% nondigestible fat and is fortified with food-additive ingredients. The process taught by Zimmerman is for food production, primarily with vitamins, and there is a focus on the fact that "the edible fat is a non-digestible fat" such as olestra; the purpose of these fats is that they are a fat substitute used for a cholesterol-lowering diet. The suspension taught by Zimmerman is not suitable for use a nutrient supplement, let alone an iron nutrient supplement.

U.S. Pat. No. 3,992,556 [Kovacs et al. (Kovacs)] teaches a particulate food supplement composition comprising a nutrient such as assimilable iron compounds, vitamins, minerals or mixtures thereof which nutrient is uniformly dispersed in a carrier consisting essentially of particles or beads of an edible metabolizable fat. Notably, the edible fat is solid at room temperature, with a preferred softening or melting point between about 100° and 250° F., whereby the assimilable iron compounds, vitamins, minerals or mixtures thereof can be conveniently added or applied to a variety of foods, such as breakfast food cereals, crackers, cookies, potato chips and similar snack foods, flour and pasta during their productions. The particulate food supplement taught by Kovacs is not suitable for use a liquid (room temperature) nutrient supplement, let alone a liquid (room temperature) iron nutrient supplement.

One of the difficulties associated with the prior art approaches to adequate iron supplementation is the poor adherence of people to taking an iron supplement. This is partly the result of the unpleasant nature of currently available liquid iron products. Iron in solution has an unpleasant taste, which manufacturers try to mask by adding flavoring materials. Conventionally, liquid iron supplements involve the use of an eyedropper to draw up the liquid from a bottle, and this liquid is then transferred either directly into the mouth or mixed with food or a drink.

In the case of a breast-feeding infant, the present inventor is not aware of a satisfactory manner by which to give an iron supplement. Pills and powdered products are disadvantageous because babies can neither chew them nor eat the food to which they are added. The American Academy of Pediatrics specifies that "liquid iron supplements" should be provided to infants between 6-12 months of age if they are even partially breast fed. For preterm infants, the American Academy of Pediatrics recommends an iron intake of at least 2 mg/kg per day through 12 months of age. Preterm infants fed human milk should receive an iron supplement of 2 mg/kg per day by 1 month of age, and this should be continued until the infant is weaned or begins eating foods that supply the 2 mg/kg of iron (Baker 2010 APA).

Existing water-based iron products for infants require the use of an eyedropper. Although the existing liquid iron products are referred to as "drops", this is a misnomer, because the typical dosage is about 1 milliliter (equivalent to about 30 drops) measured out with an eyedropper. These products are difficult to administer and their taste is commonly something that an adult or infant will find unpleasant. This results in skipped and missed doses, and as a result, inadequate supplementation with iron.

Thus, there remains a need in the art for liquid (at room temperature/20° C.) iron supplement that is readily administrable to a human, particularly an infant.

SUMMARY OF THE INVENTION

It is an object of the present invention to obviate or mitigate at least one of the above-mentioned disadvantages of the prior art.

It is another object of the present invention to provide a novel composition that is useful as a dietery supplement.

Accordingly, in one of its aspects, the present invention provides a composition comprising: (i) a non-encapsulated iron salt, and (ii) a carrier comprising digestible edible oil that is a liquid at 20° C.

In another of its aspects, the present invention relates to use of the above-mentioned composition as a dietery supplement.

In yet another of its aspects, the present invention relates to a delivery system for dispensing the above-mentioned composition.

In yet another of its aspects, the present invention relates to use of the above-mentioned delivery system to dispense the above-mentioned composition as a dietery supplement.

In yet another aspect of the present invention, this is provided a composition comprising finely powdered salts of iron in a suspension in edible oil. This is provided in a vial that is capped with a vertical-dropper dispenser plug, also known as a Eurodropper, as illustrated FIG. 1. The dose of iron can be dispensed by counting out fewer than 30 drops, ideally about 1-5 drops.

In yet another aspect of the present invention, there is provided a method for preventing iron deficiency anemia in a mammal, comprising the steps of providing a therapeutically effective amount of the iron suspension in a pharmaceutically acceptable liquid lipid based excipient to the mammal.

In yet another aspect of the present invention there is provided an article of manufacture comprising packaging material, preferably a glass vial, and a pharmaceutical composition contained therein, wherein said pharmaceutical composition is therapeutically effective to prevent or treat iron deficiency anemia. Preferably, the packaging material comprises a vial into the opening of which is inserted a Eurodropper fitting to dispense individual drops, a screw cap to completely enclose the contents. The contents comprise one or more finely powdered iron salts in an edible oil.

The present composition advantageously provides iron in a form that is easily administered to an infant or adult. When taken directly by mouth or added to food or infant formula, the composition has a desirably bland flavor and is easy to consume. Moreover, the high density of iron per unit volume of the composition results in a minimal volume of liquid to be administered. This makes the composition relatively innocuous and easy for infants to consume.

In yet another aspect of the present invention there is provided an article of manufacture comprising packaging material, preferably a glass or squeezable plastic vial, and a pharmaceutical composition contained therein, wherein said pharmaceutical composition is therapeutically effective to prevent or treat iron deficiency anemia. Preferably, the packaging material comprises capped vial that is first shaken, and then from which suspension is drawn up using a calibrated eyedropper or a syringe. Alternatively, the packaging material is a plastic vial capped with a dropper nozzle, whereby after shaking, the vial can be inverted and drops counted as they are squeezed from the vial.

Thus, the present inventor has discovered a composition which is particularly suitable for administration of iron to infants, but also suitable for children and adults. One aspect of the present invention is a liquid suspension of iron salts in edible oil in a composition that makes it suitable for a product that drips properly from a vial that has a vertical, so-called Eurodropper dispenser dropper affixed to it—see FIG. 1. Alternatively, the present composition may be drawn up into a syringe or an eyedropper for administration, for example, to a human. It has been discovered that suspensions of non-encapsulated salts of iron in oil can be manufactured to provide milligram amounts of elemental iron per drop. In addition, the present composition has a desirably bland taste and behaves in a manner suitable for delivery with a convenient, reliable and safe, inverted-dropper (e.g., Eurodropper or plastic squeeze-bottle) format.

Preferably, the present composition is in the form of a concentrated iron suspension in oil, more preferably having one or more of the following features:
  The suspension is dense enough so that no more than 30 drops deliver the dose of iron for a day. i.e. about 60 mg elemental iron per mL
  The preparation has essentially no flavour.
  The concentration of the suspension is consistent from start to end of bottle. It is neither so thick or so sticky that it fails to drip consistently from the Eurodropper dispenser. For example, water can suspend the iron salt, but the salt settles so fast at the nozzle of the Eurodropper, that what comes out looks and behaves like a drop of mud. Lipid-encapsulated iron powder was impractical in an oil excipient (e.g., Zlotkin described above), probably because the lipid encapsulation formed a sticky sediment that failed to resuspend the iron particles in a manner suitable for dispensing a dose with a dropper.

BRIEF DESCRIPTION OF THE DRAWINGS

Embodiments of the present invention will be described with reference to the accompanying drawings, wherein like reference numerals denote like parts, and in which:

FIG. 1 illustrates a preferred delivery system for dispense the present composition.

DETAILED DESCRIPTION OF THE PREFERRED EMBODIMENTS

Broadly, in one of its aspects, the present invention relates to a composition comprising: (i) a non-encapsulated iron salt, and (ii) a carrier comprising digestible edible oil that is a liquid at 20° C. Preferred embodiments of the composition may include any one or a combination of any two or more of any of the following features:
  the non-encapsulated iron salt is selected from the group consisting of ferrous fumarate, ferrous succinate, ferrous gluconate, ferric pyrophosphate, ferric saccharate, ferric orthophosphate, ferrous sulfate and mixtures of two or more of these;

the non-encapsulated iron salt is ferrous fumarate;
the digestible edible oil is a naturally occurring oil;
the digestible edible oil is a vegatable oil;
the digestible edible oil is selected from the group consisting of fractionated palm oil, coconut oil, olive oil, sesame oil, borage oil, canola oil, corn oil, almond oil, peanut oil, castor oil, cottonseed oil, rapeseed oil, sesame seed oil, fractionated components of any of these and mixtures of two or more of these;
the digestible edible oil is a triglyceride oil;
the digestible edible oil is a medium chain triglyceride oil;
the digestible edible oil is a medium chain triglyceride oil have at least 90% by weight $C_6$-$C_{12}$ triglycerides;
the digestible edible oil is a medium chain triglyceride oil have at least 95% by weight $C_6$-$C_{12}$ triglycerides;
the digestible edible oil is a medium chain triglyceride oil have at least 90% by weight $C_8$-$C_{10}$ triglycerides;
the digestible edible oil is a medium chain triglyceride oil have at least 95% by weight $C_8$-$C_{10}$ triglycerides;
the medium chain triglyceride oil is substantially completely unsatured;
the carrier comprises a mixture of the medium chain triglyceride oil and non-fractionated edible oil;
the medium chain triglyceride oil is present in an amount of from about 10% to about 90% by weight and the non-fractionated edible oil makes up the balance of the mixture;
the non-encapsulated iron salt is present in an amount to provide at least about 25 mg elemental iron/mL digestible edible oil;
the non-encapsulated iron salt is present in an amount to provide from about 25 mg elemental iron/mL digestible edible oil to about 150 mg elemental iron/mL digestible edible oil;
the non-encapsulated iron salt is present in an amount to provide from about 40 mg elemental iron/mL digestible edible oil to about 120 mg elemental iron/mL digestible edible oil;
the non-encapsulated iron salt is present in an amount to provide from about 40 mg elemental iron/mL digestible edible oil to about 100 mg elemental iron/mL digestible edible oil;
the non-encapsulated iron salt is present in an amount to provide from about 60 mg elemental iron/mL digestible edible oil to about 70 mg elemental iron/mL digestible edible oil;
the composition further comprises at least one supplemental nutrient;
the supplemental nutrient is a vitamin;
the supplemental nutrient is a fat-soluble vitamin;
the supplemental nutrient is selected from the group consisting of vitamin D, vitamin E, vitamin K and mixtures of two or more of these; and/or
the supplemental nutrient is vitamin D.

In another of its aspects, the present invention relates to use of the above-described composition a dietery supplement. Preferred embodiments of this use may include any one or a combination of any two or more of any of the following features:
use of the to prevent iron deficiency in a mammal;
use of the composition to prevent iron deficiency in a human;
use of the composition to prevent iron deficiency in a human infant;
use of the composition to treat iron deficiency in a mammal;
use of the composition to treat iron deficiency in a human;
use of the composition to treat iron deficiency in a human infant;
use wherein the composition is initially applied to a physical surface;
the physical surface is a pacifier;
the physical surface is a human breast;
the physical surface is a human nipple;
the physical surface is a foodstuff;
the physical surface is a solid foodstuff; and/or
the physical surface is a liquid foodstuff.
the physical surface is human skin, such as a clean finger used to wipe the iron suspension into the mouth of an infant
the physical surface is human skin, such as the back of a hand from which the iron suspension is licked into the mouth In another of its aspects, the present invention relates to a delivery system comprising a housing containing the above-described composition, the housing configured to dispense the composition. Preferred embodiments of this delivery system may include any one or a combination of any two or more of any of the following features:
the housing comprises a nozzle that is configured to dispense at least one drop of the composition;
the housing comprises a nozzle that is configured to dispense multiple drops of the composition;
the housing comprises a nozzle that is configured to dispense only a single drop of the composition;
the housing comprises a nozzle that is configured to dispense at least one drop of the composition when the housing is inverted;
the housing comprises a nozzle that is configured to dispense multiple drops of the composition when the housing is inverted;
the housing comprises a nozzle that is configured to dispense only a single drop of the composition when the housing is inverted;
the delivery system is in the form of a dropper bottle;
the delivery system is in the form of an eye-dropper;
the delivery system is in the form of a syringe; and/or
the delivery system is in the form of a squeeze bottle.

In another of its aspects, the present invention relates to use of the above-described delivery system to dispense the above-mentioned composition as a dietery supplement. Preferred embodiments of this use may include any one or a combination of any two or more of any of the following features:
use of the to prevent iron deficiency in a mammal;
use of the composition to prevent iron deficiency in a human;
use of the composition to prevent iron deficiency in a human infant;
use of the composition to treat iron deficiency in a mammal;
use of the composition to treat iron deficiency in a human;
use of the composition to treat iron deficiency in a human infant;
use wherein the composition is initially applied to a physical surface;
the physical surface is the exterior of a pacifier;
the physical surface is a human breast;
the physical surface is a human nipple;
the physical surface is a human finger;
the physical surface is a foodstuff;
the physical surface is a solid foodstuff; and/or
the physical surface is a liquid foodstuff.

The present invention, inter alia, provides a composition and delivery system useful to the prevention and treatment of iron deficiency anemia. Preferably, the composition is in the form of a suspension of iron in an edible, digestible oil contained within a vial to the opening of which is inserted Eurodropper plug.

As used throughout this specification, the term "prevent" is used to describe the capacity of the composition to lessen the risk of iron deficiency anemia, and may also refer to the therapy to prevent or treat one or more of the adverse effects associated with iron deficiency.

As used throughout this specification, the term "edible oil" is used to refer to edible and digestible oil, which is liquid at room temperature (20° C.). The edible oil will suspend granules of one or more salts of iron that are not encapsulated, but that may or may not be micro-encapsulated. The oil serves as an excipient. Examples of such oils include mono-, di- and triglycerides, especially extracted edible oils in hydrogenated form such as vegetable oil, castor oil, cotton seed oil, corn oil, canola oil, rape seed oil, peanut oil, sesame seed oil, coconut oil and mixtures thereof, as well as fractionated components isolated from such oils, particularly medium-chain triglycerides.

The iron of the present composition may comprise any bioavailable solid form of iron including such salts of iron as ferrous fumarate, ferrous sulfate, ferrous gluconate, ferrous succinate, ferric pyrophosphate, serric saccharate, ferric ortho phosphate or any other compound capable of providing bioavailable iron preferably without encapsulation, but also including microencapsulated forms of the compounds listed here.

The present composition may be supplemented with additional micronutrients, which may function independently of iron to serve the nutritional needs of mammals. In a preferred embodiment, vitamin D would be included as a component.

A method for use of the present composition to prevent or to treat iron deficiency in a mammal is also provided. The method involves the steps of adding a therapeutically effective amount of the composition to a food, or directly into the mouth of a mammal or on to an exterior surface to be licked or sucked off. This method starts by having the liquid composition within a Eurodropper stoppered vial, sealed with a screw top cap. To suspend the iron powder, the vial is shaken vigorously by holding the vial by its cap and swinging it back and forth like an old-fashioned fever thermometer, the screw top is removed, the vial is held upside down to permit one or more drops of the iron suspension to be released from the nozzle portion of the Eurodropper. After the dose is dispensed, the vial is placed upright and the cap closure is reapplied to the vial. The one or more drops released contain the desired amount of elemental iron and can be taken directly into the mouth, or applied to an exterior surface and sucked, or added to food, infant formula or a beverage, or applied to a finger and wiped into the mouth (for example, wiped inside the cheek of an infant).

In a highly preferred embodiment of the present composition, the carrier comprises a medium chain triglyceride oil—e.g., medium chain triglyceride oil substantially comprising $C_6$-$C_{12}$ triglycerides (see above).

Medium-chain triglyceride oils are conventionally obtained from the oil extracted from the hard, dried fraction of the endosperm of *Cocos nucifera* L. or from the dried endosperm of *Elaeis guineensis* Jacq. They consist of a mixture of triglycerides of saturated fatty acids, mainly of caprylic acid ($C_8H_{16}O_2$) and of capric acid ($C_{10}H_{20}O_2$). They contain not less than 95 percent of saturated fatty acids having 8 to 10 carbon atoms. The oil is a clear solution.

In a highly preferred embodiment, the fatty acid fraction of medium-chain triglyceride has the following composition:

| Carbon-Chain Length | Number of Double Bonds | Percentage (%) |
| --- | --- | --- |
| 6 | 0 | ≤2.0 |
| 8 | 0 | 50.0-8.0 |
| 10 | 0 | 20.0-50.0 |
| 12 | 0 | ≤3.0 |
| 14 | 0 | ≤1.0 |

Preferred embodiments of the present invention will be described with reference to following examples which should not be used to construe or limit the invention.

Example 1

Iron salt in the form of ferrous sulfate (dried) and ferrous fumarate were investigated for dispersibility and settling behavior in a range of carrier liquids. Sufficient iron salt was added to test tubes to achieve concentrations of elemental iron equivalent to 66 mg/mL suspension (i.e., 2 mg/drop, a commercially-viable concentration for infant supplementation). Each iron salt species was tested in liquids of differing viscosity—the results are provided in Table 1.

TABLE 1

| Carrier Liquid | Viscosity (cP@ 20° C.) | Density (g/cm$^3$) |
| --- | --- | --- |
| Water | 1 | 1 |
| Medium chain triglyceride | 27-33 | 0.95 |
| Olive oil | 83.3 | 0.92 |
| Rapeseed oil | 230-270 | 0.91 |

The initial preparation of dry powder iron salts into suspension was achieved by weighing the desired amount of dry powder, which was added to the liquid in a capped test tube. The combination was shaken for about two minutes, and it was then allowed to settle overnight to promote thorough particle whetting.

Suitability of the preparation for suspension was next tested by counting the number inversions of the test tube inversions required to achieve an even dispersion of particles in the carrier liquid. Each replicate began with iron salt fully settled at the bottom of the test tube.

Settling behavior was also tested for each carrier liquid. Test tubes of carrier liquid were loaded with either ferrous sulfate (dried) or ferrous fumarate at concentrations of 66 mg/mL of elemental iron. An even dispersion was achieved with inversion and shaking. Settling was then allowed to proceed and the time required for the iron salt particulate to show evidence of settling was recorded. Evidence of settling was considered as a reduction in opacity throughout the top 1 cm of liquid in the test tube.

The results for both dispersion and settling experiments are provided in Table 2.

TABLE 2

| | Dispersion (# of inversions) | | Settling (seconds) | |
| --- | --- | --- | --- | --- |
| Carrier Liquid | Ferrous sulfate (dried) | Ferrous fumarate | Ferrous sulfate (dried) | Ferrous fumarate |
| Medium chain triglyceride | 7.3 ± 0.6 | 56.4 ± 10.6 | 42.3 ± 8.5 | 16.3 ± 1.2 |

TABLE 2-continued

|  | Dispersion (# of inversions) | | Settling (seconds) | |
| --- | --- | --- | --- | --- |
| Carrier Liquid | Ferrous sulfate (dried) | Ferrous fumarate | Ferrous sulfate (dried) | Ferrous fumarate |
| Rapeseed oil | 62.0 ± 6.0 | 167.0 ± 7.0 | 238.7 ± 5.9 | 144.0 ± 5.7 |
| Olive oil | 27.3 ± 4.5 | 84.0 ± 1.4 | 213.3 ± 7.6 | 95.5 ± 4.9 |
| Water | N/A | 4.3 ± 0.6 | N/A | 1.0 ± 0.5 |

A balance of rapid dispersion with slow settling is preferred for the present composition. Settling is inevitable for such a product given a shelf life in the range of months to years. Maintenance of an iron salt dispersion over this time period would require a prohibitively-thick carrier liquid (with viscosity in excess of 2,000 cp). As such, rapid dispersibility is also a preferred feature to ensure even distribution of iron salt throughout the carrier immediately prior to drop-wise dispensation.

It was found that medium chain triglyceride oil exhibited acceptably rapid ferrous fumarate dispersibility relative to the other carriers. Water-based preparations tended to disperse either very easily (ferrous fumarate) or not at all (ferrous sulfate (dried), likely due to development of an interfacial layer of ferrous sulfate heptahydrate on the settled iron salt). Ferrous fumarate in water also exhibited extremely rapid settling. Rapeseed and olive oils carriers held both suspensions well (each settling at >90 seconds) but required 1.5-3 times more agitation to achieve dispersion—consequently, these oils can be used as carriers but a less preferred than medium chain triglyceride oil.

Example 2

Drop consistency was examined to determine suitability of various dispersions for Eurodropper dispensing. Preparations of various iron salts, at concentrations of 66 mg/mL, were made using medium chain triglyceride oil. Each sample was shaken vigorously and then inverted to dispense 10 drops. This was repeated until 60 drops were dispensed. The results for the average drop size are reported in Table 3.

TABLE 3

| Iron Salt (particle size) | Average 10 Drop Weight (mg ± SD) |
| --- | --- |
| Ferrous fumarate (Sigma, XXX μm) | 264.7 ± 10.2 |
| Ferrous fumarate (Watson, 149 μm) | 277.0 ± 10.3 |
| Ferrous pyrophosphate | 266 * |
| Ferrous sulfate (dried) | N/A ** |

* Dispersion failed to dispense from the Eurodropper after 15 drops.
** Dispersion failed to dispense at all from the Eurodropper because the powder clumped in the oil, and occluded opening.

The effect of carrier liquid type on drop consistency was next examined. Preparations of ferrous fumarate (149 μm particle size) were prepared and drop consistency was measured using similar methodology to that described above. The results for the average drop size are reported in Table 4.

| Iron Salt | Average 10 Drop Weight (mg ± SD) |
| --- | --- |
| Medium chain triglyceride | 276.2 ± 3.0 |
| Canola oil | 284.8 ± 4.7 |
| Olive oil | 285.8 ± 3.5 |
| Water | Occluded * |

* Dispersion failed to dispense at all from the Eurodropper, since suspension settled so quickly, it occluded the opening out of the dropper bottle.

Ferrous fumarate has shown to be a particularly suitable iron salt in terms of consistent performance in the Eurodropper regardless of carrier liquid. The viscosity carrier liquid edible oil can also be adjusted to optimize the quality of the product by combining one or more other edible oils, such as bees wax as a thickener Example 3

It is well known that edible oil is susceptible to oxidation, producing off-flavor compounds and decreasing oil quality (Choe and Min, Comprehensive Reviews in Food Science and Food Safety 2006 Vol 5:169-186). Vegetable oils are known to contain iron that is of particular concern because it catalyzes oxidation of the oils.

Susceptibility of medium-chain triglyceride oil to lipid peroxidation was examined in the absence and presence of 75 mg/mL elemental iron as ferrous fumarate (225 mg ferrous fumarate per mL). Oil without and with iron was prepared, 10-mL in 15-mL amber glass vials, capped with a Eurodropper cap, and incubated at 40 degrees Centigrade for accelerated stability testing, as is commonly done in the pharmaceutical industry to confirm the suitability of a product.

Analyses of product stability and quality were done according to United States Pharmacopea (USP 34) methods. The results are reported in Table 5.

TABLE 5

| ACCELERATED STABILITY TESTING OF FERROUS FUMARATE IN OIL* | | | | | | | |
| --- | --- | --- | --- | --- | --- | --- | --- |
| Iron (mg/mL) | Claimed content of iron | | 0 | 75 | 0 | 75 | 0 | 75 |
| Time (months) | at 40 C. Temp | | 0 | 0 | 2 | 2 | 6 | 6 |
| TEST | METHOD | SPECIFICATION | RESULTS | | | | | |
| Iron (% of claim) | USP(1) | 90-120 | NA | 101 | NA | 94 | NA | 106 |
| Peroxide value | USP<401> | <5 meq/Kg | 0 | 2 | 0 | 4 | 0 | 1 |
| p-Anisidine value | USP<401> | <16 meq/Kg | 0 | <.2 | 1 | 0.3 | 0 | 0.04 |
| Total oxidation | USP<401> | <26 meq/Kg | 0 | 4 | 2 | 8 | 0 | 2 |

*NA indicates the percentage value is not applicable, since there was no iron present Surprisingly, all of the results of testing remained within USP specifications throughout the 6 months of testing. Ferrous fumarate suspension in medium chain triglyceride has thus shown to be a suitable iron salt in terms of stability and resistance to oil oxidation. Although other oils and salts were not tested in a similar manner, based on the results in Table 5 it could be expected that other oils and iron salts can also be found to be suitable.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A composition consisting of:
a non-encapsulated iron salt; and
a carrier of a digestible edible oil that is a liquid at 20° C.

2. The composition defined in claim 1, wherein the digestible edible oil is a medium chain triglyceride oil having at least 90% by weight $C_6$-$C_{12}$ triglycerides.

3. The composition defined in claim 1, wherein the digestible edible oil is a medium chain triglyceride oil having at least 90% by weight $C_8$-$C_{10}$ triglycerides.

4. The composition defined in claim 1, wherein the non-encapsulated iron salt is present in an amount to provide at least about 25 mg elemental iron/mL digestible edible oil.

5. The composition defined in claim 1, wherein the non-encapsulated iron salt is present in an amount to provide from about 40 mg elemental iron/mL digestible edible oil to about 100 mg elemental iron/mL digestible edible oil.

6. Use of the composition defined in claim 1 to prevent iron deficiency in a human infant, wherein said use comprises dispensing at least one drop of said composition to a physical surface, and having said human infant consume said composition from said physical surface.

7. Use of the composition defined in claim 1 to treat iron deficiency in a human infant, wherein said use comprises dispensing at least one drop of said composition to a physical surface, and having said human infant consume said composition from said physical surface.

8. The use defined in claim 6, wherein the composition comprising: (i) a non-encapsulated iron salt, and (ii) a carrier comprising digestible edible oil that is a liquid at 20° C. is initially applied to an exterior physical surface.

9. A delivery system comprising a housing containing the composition defined in claim 1, the housing configured to dispense the composition.

10. The delivery system defined in claim 9, wherein the housing comprises a nozzle that is configured to dispense at least one drop of the composition when the housing is inverted.

11. The delivery system defined in claim 9, wherein the housing comprises a nozzle that is configured to dispense only a single drop of the composition when the housing is inverted.

12. The delivery system defined in claim 9, in the form of a dropper bottle.

* * * * *